United States Patent
Nycz et al.

(10) Patent No.: US 8,095,198 B2
(45) Date of Patent: Jan. 10, 2012

(54) METHODS FOR DETECTING OSTEOLYTIC CONDITIONS IN THE BODY

(75) Inventors: Jeffrey H. Nycz, Collierville, TN (US); Susan J J. Drapeau, Cordova, TN (US); William T. Donofrio, Andover, MN (US)

(73) Assignee: Warsaw Orthopedic. Inc., Warsaw, IN (US)

( * ) Notice: Subject to any disclaimer, the term of this patent is extended or adjusted under 35 U.S.C. 154(b) by 349 days.

(21) Appl. No.: 11/344,459

(22) Filed: Jan. 31, 2006

(65) Prior Publication Data
US 2007/0179568 A1 Aug. 2, 2007

(51) Int. Cl.
*A61B 5/05* (2006.01)
(52) U.S. Cl. .................... 600/348; 606/70; 600/587
(58) Field of Classification Search ............ 607/60; 600/549, 587
See application file for complete search history.

(56) References Cited

U.S. PATENT DOCUMENTS

| | | | |
|---|---|---|---|
| 3,181,528 A | 5/1965 | Brackin | |
| 4,016,866 A * | 4/1977 | Lawton | 600/348 |
| 4,080,653 A | 3/1978 | Barnes et al. | |
| 4,195,367 A | 4/1980 | Kraus | |
| 4,195,643 A | 4/1980 | Pratt, Jr. | |
| 4,281,667 A | 8/1981 | Cosman | |
| 4,407,296 A | 10/1983 | Anderson | |
| 4,430,999 A | 2/1984 | Brighton et al. | |
| 4,519,394 A | 5/1985 | Black et al. | |
| 4,519,401 A | 5/1985 | Ko et al. | |
| 4,672,963 A | 6/1987 | Barken | |
| 4,781,181 A | 11/1988 | Tanguy | |
| 4,785,822 A | 11/1988 | Wallace | |
| 4,813,435 A | 3/1989 | Arms | |
| 4,846,191 A | 7/1989 | Brockway et al. | |
| 4,990,161 A * | 2/1991 | Kampner | 623/18.11 |
| 4,993,428 A | 2/1991 | Arms | |
| 5,083,573 A | 1/1992 | Arms | |
| 5,125,408 A | 6/1992 | Basser | |
| 5,178,148 A | 1/1993 | Lacoste et al. | |
| 5,188,109 A | 2/1993 | Saito | |
| 5,306,306 A | 4/1994 | Bisek et al. | |
| 5,360,016 A | 11/1994 | Kovacevic et al. | |
| 5,360,452 A * | 11/1994 | Engelhardt et al. | 623/22.37 |
| 5,394,875 A | 3/1995 | Lewis et al. | |
| 5,413,116 A | 5/1995 | Radke et al. | |
| 5,425,775 A | 6/1995 | Kovacevic et al. | |
| 5,456,724 A | 10/1995 | Yen et al. | |
| 5,470,354 A | 11/1995 | Hershberger et al. | |
| 5,480,439 A | 1/1996 | Bisek et al. | |
| 5,533,519 A | 7/1996 | Radke et al. | |
| 5,535,752 A | 7/1996 | Halperin et al. | |

(Continued)

FOREIGN PATENT DOCUMENTS

DE 10342823 4/2005

(Continued)

OTHER PUBLICATIONS

Ulrike Klueh, et al.; *Enhancement of implantable glucose sensor function in vivo using gene transfer-induced neovascularization*; Biomaterials 26 (2005) 1155-1163; Jun. 7, 2004.

(Continued)

*Primary Examiner* — Max Hindenburg
*Assistant Examiner* — Renee Danega

(57) ABSTRACT

Methods and systems for detecting a biological response indicative of osteolysis or osteolytic pre-conditions in bone.

30 Claims, 4 Drawing Sheets

U.S. PATENT DOCUMENTS

| | | | |
|---|---|---|---|
| 5,564,434 A | 10/1996 | Halperin et al. | |
| 5,651,767 A | 7/1997 | Schulman et al. | |
| 5,695,496 A | 12/1997 | Orsak et al. | |
| 5,720,771 A | 2/1998 | Snell | |
| 5,759,199 A | 6/1998 | Snell et al. | |
| 5,810,735 A | 9/1998 | Halperin et al. | |
| 5,935,171 A | 8/1999 | Schneider et al. | |
| 5,984,875 A | 11/1999 | Brune | |
| 5,993,395 A | 11/1999 | Shulze | |
| 6,034,296 A | 3/2000 | Elvin et al. | |
| 6,059,784 A | 5/2000 | Perusek | |
| 6,074,394 A | 6/2000 | Krause | |
| 6,125,290 A | 9/2000 | Miesel | |
| 6,144,866 A | 11/2000 | Miesel et al. | |
| 6,171,252 B1 | 1/2001 | Roberts | |
| 6,185,452 B1 | 2/2001 | Schulman et al. | |
| 6,208,894 B1 | 3/2001 | Schulman et al. | |
| 6,221,024 B1 | 4/2001 | Miesel | |
| 6,223,081 B1 | 4/2001 | Kerver | |
| 6,245,109 B1 | 6/2001 | Mendes et al. | |
| 6,248,080 B1 | 6/2001 | Miesel et al. | |
| 6,285,897 B1 | 9/2001 | Kilcoyne et al. | |
| 6,433,629 B2 | 8/2002 | Hamel et al. | |
| 6,447,448 B1 | 9/2002 | Ishikawa et al. | |
| 6,450,946 B1 | 9/2002 | Forsell | |
| 6,454,699 B1 | 9/2002 | Forsell | |
| 6,454,700 B1 | 9/2002 | Forsell | |
| 6,503,249 B1 | 1/2003 | Krause | |
| 6,529,127 B2 | 3/2003 | Townsend et al. | |
| 6,546,268 B1 | 4/2003 | Ishikawa et al. | |
| 6,573,706 B2 | 6/2003 | Mendes et al. | |
| 6,582,365 B1 | 6/2003 | Hines et al. | |
| 6,583,630 B2 | 6/2003 | Mendes et al. | |
| 6,585,647 B1 | 7/2003 | Winder | |
| 6,610,096 B2 | 8/2003 | MacDonald | |
| 6,615,067 B2 | 9/2003 | Hoek et al. | |
| 6,638,231 B2 | 10/2003 | Govari et al. | |
| 6,656,135 B2 | 12/2003 | Zogbi et al. | |
| 6,689,056 B1 | 2/2004 | Kilcoyne et al. | |
| 6,695,885 B2 | 2/2004 | Schulman et al. | |
| 6,706,005 B2 | 3/2004 | Roy et al. | |
| 6,712,772 B2 | 3/2004 | Cohen et al. | |
| 6,714,763 B2 | 3/2004 | Hamel et al. | |
| 6,733,458 B1 | 5/2004 | Steins et al. | |
| 6,761,741 B2 | 7/2004 | Iesaka | |
| 6,783,499 B2 | 8/2004 | Schwartz | |
| 6,802,811 B1 | 10/2004 | Slepian | |
| 6,821,299 B2 * | 11/2004 | Kirking et al. | 623/20.14 |
| 6,849,463 B2 | 2/2005 | Santini, Jr. et al. | |
| 6,889,165 B2 | 5/2005 | Lind et al. | |
| 7,190,273 B2 * | 3/2007 | Liao et al. | 340/573.1 |
| 2002/0016719 A1 * | 2/2002 | Nemeth et al. | 705/2 |
| 2002/0049394 A1 | 4/2002 | Roy et al. | |
| 2002/0107649 A1 | 8/2002 | Takiguchi et al. | |
| 2002/0151894 A1 | 10/2002 | Melkent et al. | |
| 2002/0198526 A1 | 12/2002 | Shaolian et al. | |
| 2003/0032874 A1 | 2/2003 | Rhodes et al. | |
| 2003/0069644 A1 | 4/2003 | Kovacevic et al. | |
| 2003/0105470 A1 | 6/2003 | White | |
| 2003/0139690 A1 | 7/2003 | Aebli et al. | |
| 2003/0186914 A1 | 10/2003 | Hofer et al. | |
| 2003/0199783 A1 * | 10/2003 | Bloom et al. | 600/549 |
| 2004/0011671 A1 | 1/2004 | Shults et al. | |
| 2004/0059423 A1 | 3/2004 | Barnes et al. | |
| 2004/0143302 A1 | 7/2004 | Sieracki et al. | |
| 2004/0176672 A1 | 9/2004 | Siler et al. | |
| 2004/0186396 A1 * | 9/2004 | Roy et al. | 600/594 |
| 2004/0197267 A1 | 10/2004 | Black et al. | |
| 2004/0204744 A1 | 10/2004 | Penner et al. | |
| 2004/0230115 A1 | 11/2004 | Scarantino et al. | |
| 2004/0236192 A1 | 11/2004 | Necola et al. | |
| 2005/0010299 A1 | 1/2005 | Disilvestro | |
| 2005/0010300 A1 | 1/2005 | Disilvestro et al. | |
| 2005/0010301 A1 | 1/2005 | Disilvestro et al. | |
| 2005/0010302 A1 | 1/2005 | Dietz et al. | |
| 2005/0012610 A1 | 1/2005 | Liao et al. | |
| 2005/0012617 A1 | 1/2005 | Disilvestro et al. | |
| 2005/0103625 A1 | 5/2005 | Rhodes et al. | |
| 2005/0107677 A1 | 5/2005 | Ward et al. | |
| 2005/0119587 A1 | 6/2005 | Roessler et al. | |
| 2005/0124873 A1 | 6/2005 | Shults et al. | |
| 2005/0228247 A1 | 10/2005 | Scarantino et al. | |
| 2005/0242479 A1 | 11/2005 | Petisce et al. | |
| 2005/0245795 A1 | 11/2005 | Goode, Jr. et al. | |
| 2005/0245799 A1 | 11/2005 | Brauker et al. | |
| 2005/0251033 A1 | 11/2005 | Scarantino et al. | |
| 2006/0047283 A1 * | 3/2006 | Evans et al. | 606/102 |
| 2006/0052782 A1 * | 3/2006 | Morgan et al. | 606/60 |
| 2006/0224088 A1 * | 10/2006 | Roche | 600/587 |
| 2006/0287678 A1 * | 12/2006 | Shafer | 607/2 |
| 2007/0060800 A1 * | 3/2007 | Drinan et al. | 600/300 |

FOREIGN PATENT DOCUMENTS

| | | |
|---|---|---|
| EP | 0344770 A | 12/1989 |
| EP | 0423420 A2 | 4/1991 |
| EP | 1238630 A | 9/2002 |
| EP | 1285640 A2 | 2/2003 |
| EP | 1285640 A3 | 2/2003 |
| EP | 1442715 A2 | 8/2004 |
| EP | 1442715 A3 | 8/2004 |
| WO | WO89/11244 | 11/1989 |
| WO | WO9217113 A | 10/1992 |
| WO | WO9733513 A | 9/1997 |
| WO | WO02/15769 | 2/2002 |
| WO | WO0230338 A | 4/2002 |
| WO | WO02/085193 | 10/2002 |
| WO | WO2005007025 A | 1/2005 |
| WO | WO2006105098 A | 10/2006 |

OTHER PUBLICATIONS

BD Biosciences: In Vivo Capture Assay (IVC); *Measuring cytokine production in vitro versus in vivo*; www.//bdbiosciences.com/pharmingen/products/display_product.php?keyID=102, Nov. 15, 2005.

Kate Y. Wang, et al.; Polyethylene particles from a hip simulator cause (45) Ca release from cultured bone; Journal of Orthopaedic Surgery, Dec. 2001.

European Patent Office, International Searching Authority, Notification of Transmittal of the International Search Report and the Written Opinion of the International Searching Authority or the Declaration, International Application No. PCT/US2007/061425, May 7, 2007, 13 pages.

European Patent Office, International Searching Authority, Notification of Transmittal of the International Search Report and the Written Opinion of the International Searching Authority or the Declaration, International Application No. PCT/US2007/061388, May 25, 2007, 13 pages.

European Patent Office, International Searching Authority, Notification of Transmittal of the International Search Report and the Written Opinion of the International Searching Authority or the Declaration, International Application No. PCT/US2007/061446, Jul. 4, 2007, 12 pages.

European Patent Office, International Searching Authority, Notification of Transmittal of the International Search Report and the Written Opinion of the International Searching Authority or the Declaration, International Application No. PCT/US2007/062312, Jul. 5, 2007, 13 pages.

* cited by examiner

METHODS FOR DETECTING OSTEOLYTIC CONDITIONS IN THE BODY

BACKGROUND OF THE INVENTION

The present disclosure relates generally to methods and devices for detecting osteolytic conditions or pre-conditions in the body.

Human joints, such as the knee, shoulder, elbow, hip, and vertebral joints can be replaced by prostheses or implants. Such prostheses can be fixed to surrounding bone by bone ingrowth into the implant or external features that extend into the bone. Additionally, implants can be fixed in the bone with a cement agent, such as polymethylmethacrylate.

It has been determined that the debris created by the wearing of a prosthetic implant may contribute to local bone destruction and osteolysis. Unfortunately, it is difficult to detect the synthetic debris particles and/or their concentration in the body.

Loosening of the boney attachment to the implant or the cement agent and/or material debris from the wear of the prosthetic itself can cause additional problems for the patient. Thus, there remains a need for improvements in the detection of conditions that may impact bone quality.

SUMMARY OF THE INVENTION

According to certain embodiments described herein, a detection system for detecting a condition in a bone is provided.

According to one embodiment, a detection system includes an in vivo sensor, which is operable to detect a condition of a bone, and generate a signal representative of the detected condition. The sensor may detect a condition present in the bone, or adjacent to the bone.

In one embodiment, the detection system further includes a transmitter, which is operable to receive the signal from the sensor and transmit the signal. In a further embodiment, the detection system further comprises a receiver, which is operable to receive the signal from the transmitter and to enable a human intelligible display representative of the signal.

In still another embodiment, the detection system further comprises a signal processor, which is operable to receive a signal from the sensor and to transmit the signal, and a transmitter, which is operable to receive the signal from the signal processor and to transmit the signal. In a further embodiment, the detection system includes a receiver, which is operable to receive the signal from the transmitter. According to one such embodiment, the receiver includes another signal processor, which is operable to receive the signal from the receiver and to transmit the signal, and an indicator, which is operable to receive the signal from the second signal processor and enable a human intelligible display representative of the signal.

According to still other embodiments described herein, a method of detecting a condition of a bone is provided. According to one such embodiment, the method includes disposing a sensor in or adjacent to the bone, obtaining data from the sensor representative of at least one condition selected from temperature, pH, a presence of inflammatory cytokines, a presence of matrix metalloproteinases (MMPs), a presence of calcium ions and a presence of phosphate ions, and displaying the data in a human intelligible form.

The disclosure can be more clearly understood by reference to the following drawings, which illustrate exemplary embodiments thereof, and which are not intended to limit the scope of the appended claims.

The disclosure can be more clearly understood by reference to some of its specific embodiments, described in detail below, which description is not intended to limit the scope of the claims in any way.

DETAILED DESCRIPTION

Figure 1:
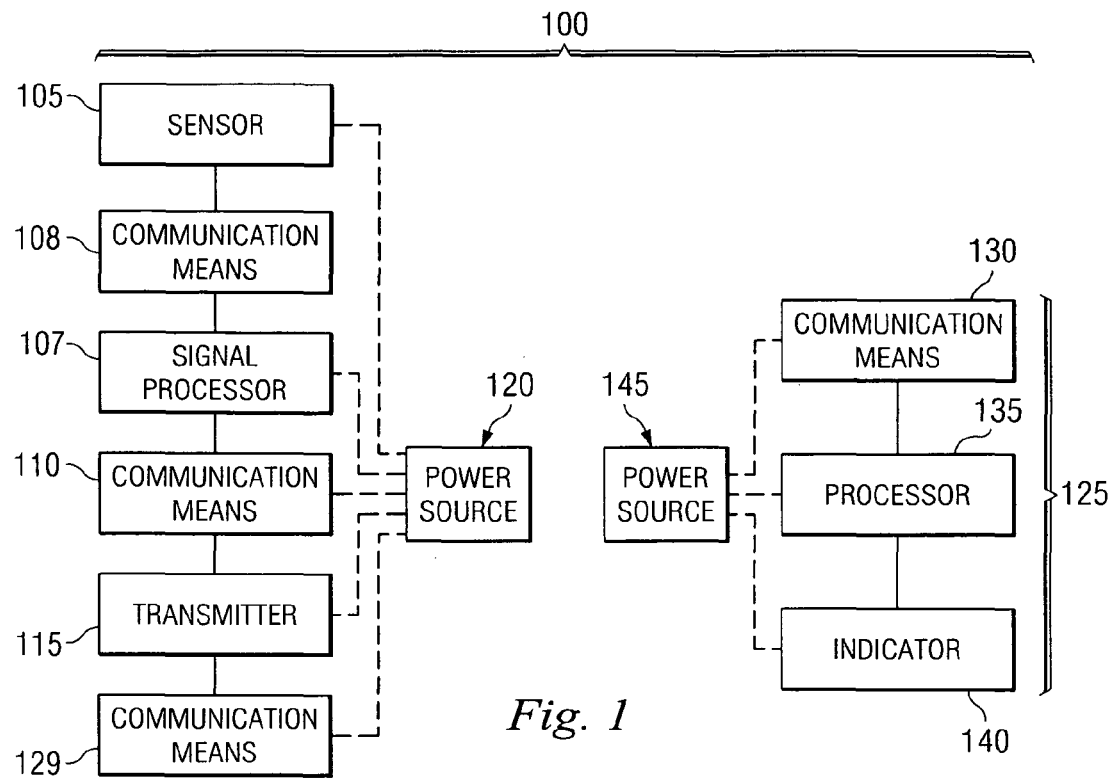
FIG. 1 is a schematic of one embodiment of a detection system as described herein.

Referring now to FIG. 1, one embodiment of a system for detecting a condition in the body according to the present disclosure is illustrated.

According to the embodiment illustrated in FIG. 1, a detection system 100 comprises a sensor 105, a signal processor 107, and a transmitter 115. The sensor 105 and the signal processor 107 are communicatively coupled by communication means 108, and the signal processor 107 and the transmitter 115 are communicatively coupled by communication means 110. Communication means 108 and 110 can be wired or wireless, as will be discussed further herein. In certain embodiments, signal processor 107 could contain a memory unit, or could be communicatively coupled to a memory unit. As will be discussed further herein, a memory unit would store data received from the signal processor.

For ease of reference, the sensor 105, signal processor 107, and transmitter 115, are illustrated separately in FIG. 1, and are discussed as separate units herein. However, it is fully contemplated that the functions of each may be combined into a single component or distributed among a plurality of components.

Sensor 105 is designed for implantation into the body of a patient. In some embodiments, sensor 105 is disposed adjacent to a prosthesis, such as a hip, knee, shoulder, wrist, jaw or vertebral implant. In some such embodiments, sensor 105 is physically associated with the prosthesis, for example, such as described in FIGS. 4-6. In other embodiments, sensor 105 is not physically associated with the prosthesis. For example, sensor 105 could be engaged in bone or embedded in soft tissue in the proximity of the prosthesis.

Sensor 105 is operable to detect conditions in bone associated with osteolysis occurring in the bone, or conditions in the bone indicative of an early onset of osteolysis ("osteolytic pre-conditions"). For example, an increase in temperature in the bone, an increase in the pH level of the bone, the presence of inflammatory cytokines (for example, TNF, IL-1, and IL-6), and the presence of certain analytes are associated with osteolysis and/or osteolytic pre-conditions. Analytes associated with osteolysis and/or osteolytic pre-conditions may include calcium ions and/or phosphate ions. Other analytes associated with osteolysis and/or osteolytic pre-conditions may include bone degradation products such as matrix metalloproteinases (MMPs), or similar bone degradation products. Still other analytes associated with osteolysis and/or osteolytic pre-conditions may include particular genes, proteins, chemicals, bacterial or similar biological substances.

Thus, a detection system as described herein could include a sensor or a plurality of sensors operable to detect one or more of a temperature increase, a pH increase, the presence of inflammatory cytokines, or the presence of a selected analyte. Accordingly, in certain embodiments, sensor 105 can be one or more of a temperature sensor (e.g., a thermocouple or a thermister), a pH sensor, a biosensor operable to detect the presence of calcium ions, a biosensor operable to detect bone degradation products or signals indicative of bone degradation, such as matrix metalloproteinases (MMPS) or similar molecules, or an in vivo assay operable to detect the presence of inflammatory cytokines. One type of pH sensor suitable for use in the detection system described herein is an iridium oxide based potentiometric electrode sold by SensIrOx Inc. Fiber optic pH sensors should also be suitable. As yet another example, sensors operable to detect the presence of ions such as calcium or phosphate could have a permeable membrane selective to the ion to be detected.

Sensor 105 will detect one or more of temperature, pH, the presence of inflammatory cytokines or the presence of an analyte, and will transmit a corresponding signal to the signal processor 107. In certain embodiments, the signal processor will receive signals from the sensor for an initial period in order to generate a baseline representative of the detected condition (e.g., a baseline for temperature, pH, presence of an analyte). After a baseline has been established, then the signal processor 107 will continue to receive signals from the sensor 105. If the signal received deviates from the baseline, then the signal processor sends a deviation signal to the transmitter 115 indicating a deviation from the baseline.

In an embodiment in which the signal processor includes or is coupled to a memory unit, data representative of the baseline can be stored. In a further embodiment, the memory unit may be configured to store data it receives from the signal processor that is either outside the normal signal range or within the range of signals being detected. In yet another embodiment, a memory unit may store data such as a timestamp of the signal, the specific characteristics of the signal, or any other relevant data. It is fully contemplated that a memory unit may utilize known compression algorithms and functions to save on memory and size requirements.

In addition, it is contemplated that two or more sensors may be used to verify readings and account for potential hardware failures in the system. The plurality of sensors may generate an aggregate baseline and deviations by one or more sensors from the aggregate baseline may cause the system to generate the deviation signal.

In other embodiments, control sensors could be positioned at locations remote from the area of interest where sensor 105 would be positioned. Signals indicative of temperature, pH, presence of inflammatory cytokines, and/or presence of analytes generated by the control sensors could be wirelessly sent to the signal processor, where the signals could be compared to signals generated by sensor 105. If the signals generated by sensor 105 deviate from the signals generated by control sensors, then the signal processor would send a signal to the transmitter 115. In still other embodiments, all signals generated by the sensor 105 are processed through the transmitter 115 without screening by the signal processor.

Transmitter 115 is adapted for receiving signals from the signal processor 107 via communication means 110. Transmitter 115 is also adapted for transmitting a signal representative of the signal received from the signal processor to a receiver 125 via communication means 129. In certain embodiments as will be discussed further with respect to FIG. 2A, receiver 125 is located outside of the patient's body, while in other embodiments, as will be discussed further with respect to FIG. 2B, receiver 125 is located within the patient's body.

Referring still to FIG. 1, in certain embodiments, communication means 129 are adapted for communicating wirelessly with communication means 130 of receiver 125. There are several types of wireless telemetry circuits that may be employed for communication means 110, 129 and 130. For example, RF, such as RFID; inductive telemetry; acoustic energy; near infrared energy; "Bluetooth"; and computer networks are all possible means of wireless communication. In one embodiment, communication means 129 and 130 are adapted for RFID communication such that communication means 129 is a passive RFID tag. Using a passive RFID tag helps limit the power requirements of communication means 129, yet still allows wireless communication to receiver 125.

In other embodiments, the transmitter comprises a modulator/transmitter that converts the voltage signal received from the sensor into a transmission signal, and transmits the converted signal to the receiver. While the specific characteristics of the internal modulator/transmitter may vary, the components will be appropriate for implantation within a patient, and will transmit a signal through the patient's body, including surrounding tissues, to the receiver.

Detection system 100 further comprises a power source 120, which is electrically connected to one or more of the sensor 105, the signal processor 107, the communication means 108, 110 or 129, and the transmitter 115. The sensor 105 can be directly electrically connected to the power source 120, or can be connected through the transmitter 115. Sensor 105 and communication means 110 may use the power source 120 to facilitate the sending of signals to the transmitter 115. Transmitter 115 may use the power source to convert signals received from the signal processor, and/or to transmit signals received from the signal processor to the receiver.

In some embodiments, power source 120 comprises a battery, for example, a lithium iodine battery similar to those used for other medical implant devices such as pacemakers. However, any type of battery suitable for implantation can be used. It is also fully contemplated that the power source 120 may include a plurality of batteries or rechargeable batteries.

In other embodiments, power source 120 may comprise a passive power supply, such as the type of power supply used in RFID tags.

In still other embodiments, the detection system may be externally powered by inductive coupling or other transmissive means from an external power supply. The detection system may also be powered by capacitor arrays, or one or more capacitors, which store the energy received from an external power supply. Additionally or alternatively, the detection system may only operate when the external power supply is energizing the system, and may be in a dormant condition when not receiving power from the external power supply.

Referring still to FIG. 1, a receiver 125 is adapted for receiving and displaying, in human intelligible form, information received from transmitter 115. Receiver 125 comprises communication means 130, a signal processor 135, and an indicator 140. In the embodiment illustrated in FIG. 1, a power supply 145 supplies power to any electrical components of the receiver 125. Such an embodiment would be preferred if the receiver is external to the patient's body, i.e., if the receiver is "ex vivo". In an embodiment where the receiver is internal to the patient's body ("in vivo"), the receiver can be powered from the same power supply as the sensor, signal processor, etc., or can be powered from a separate power supply such as is illustrated by power supply 145, which would also be located inside the patient's body.

The communication means 130 of the receiver 125 are adapted for wireless communication with the transmitter 115. Once a signal is received from the transmitter 115 by communication means 130, it is processed by processor 135, which is adapted for converting the signal into a form that may be utilized by indicator 140.

In some embodiments, the processor 135 further comprises analysis circuitry operable to evaluate the incoming signals from the transmitter 115, and determine a course of action based on those signals. For instance, the analysis circuitry can include a comparator circuit, in which the received signal is compared to a threshold value, for example, a predetermined temperature or pH. If the incoming signal exceeds the threshold value, the analysis circuit can send data to the indicator 140 or to any other display device.

Indicator 140 may be any type of device or interface that can output the data in human intelligible form, and may be composed of a plurality of output mechanisms or a single device. In certain embodiments, the indicator may be a visual display, such as a number representative of temperature or pH, a color based on temperature or pH (e.g., green for a "normal" temperature or pH, yellow for temperature or pH with moderate deviation from "normal", and red for temperature or pH indicative of the presence or onset of osteolysis), or any other visual display indicative of the desired data. For example, in an embodiment where the receiver is in vivo, at least the indicator portion of the receiver can be implanted close to the surface of the skin, such that a color can be visually observed through the skin. In an embodiment where the receiver is ex vivo, then the indicator could simply display a color.

As another example, the indicator may be a speaker. Where the indicator is a speaker it could do such things as beep or audibly speak a message representing "normal" conditions in the bone, or conditions indicative of the presence or onset of osteolysis. In an embodiment where the receiver is internal to the patient's body, at least the indicator portion of the receiver could be implanted close to the surface of the skin, such that sound generated by the indicator could be heard.

In certain embodiments, the receiver may also include a memory unit, which may be adapted for permanent or temporary storage of data obtained by the detection system. Thus, the memory unit may store data obtained at various times so that the data may later be reviewed, compared, or analyzed.

It is also contemplated that the processing performed by the processor 135 may only be a first step of processing. The processed data of the processor 135 may be output to a more powerful or specialized processing unit (not shown) where additional processing takes place. This second processing unit may be located either in the receiver itself or in a separate device such as a personal computer.

According to one such example, the data may be transferred from the processor 135 via a networking interface to a network or computer for permanent storage. The type of network utilized may include such communication means as telephone networks, computer networks, or any other means of communicating data electronically. The networking interface could obviate the need for the patient to even go into the doctor's office for obtaining conditional data on an implant. For example, the patient could obtain such data on a scheduled basis (e.g. daily, weekly, monthly, etc.). Then, utilizing the networking interface the patient could send this data to the treating doctor. The networking interface may be configured to directly access a communication network such as a telephone or computer network for transferring the data. It is fully contemplated that the computer network be accessible by a treating physician for reviewing received data without requiring the patient to make an actual visit to the doctor's office. In this regard, it is also contemplated that any communication between the receiver and the computer network may be encrypted or otherwise secured so as protect the patient's privacy.

It is also contemplated that the networking interface may be configured for communication with a separate device that is adapted for accessing the communication network. For example, the networking interface may be a USB connection. In an embodiment where the receiver is ex vivo, the receiver may be connected to a personal computer via the USB connection. The personal computer may then be utilized to connect to the communication network, such as the Internet, for transferring the data to a designated place where a treating doctor may receive it.

In some embodiments, receiver 125 can be secured on the patient, for example, strapped to an arm, leg, or the waist. In other embodiments, receiver 125 can merely be in the patient's vicinity, for example inches or feet away from the patient, as long as the broadcast range of the transmitter 115 is sufficient for receipt of signals by the receiver. In other embodiments, receiver 125 could be at a location remote from the patient, for example, a doctor's office. According to one such embodiment, the detection system could be activated only intermittently, for example, during a visit to the doctor's office. In this case, the power source for the detection system could be passive, such that it is activated by the receiver. The doctor can read data displayed by an indicator in the receiver in his or her office to determine whether signals indicative of osteolysis or an osteolytic pre-condition have been generated.

Figure 2A:
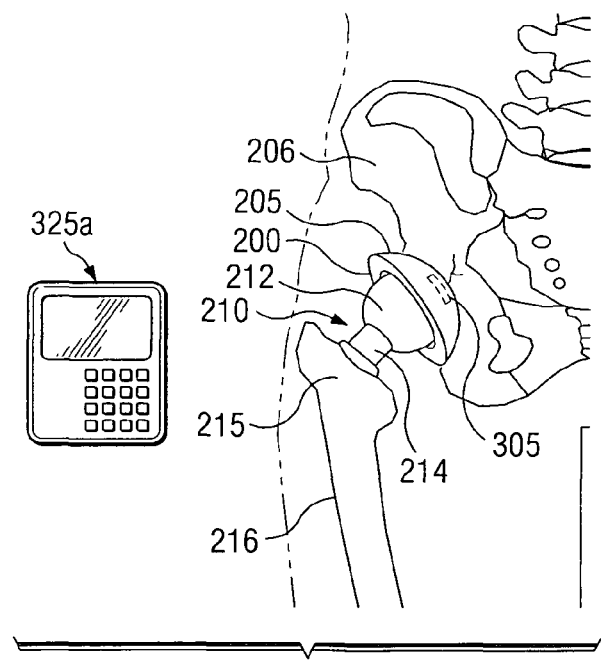
FIG. 2A is a front view of another embodiment of a detection system as described herein, which system is in use in an area where a hip prosthesis has been implanted.

Referring now to FIG. 2A, a detection system that combines the functions of the sensor 105, signal processor 107 communications means 110, transmitter 115, communications means 129, and power source 120 described in FIG. 1 into a unitary sensor 305, is illustrated in use with a hip implant 200. A memory unit could also be combined into the unitary sensor 105, either as a separate component, or within the signal processor.

Hip implant 200 includes an acetabular component 205, which is configured for engagement with a prepared portion of the patient's acetabulum 206, and a femoral component 210, which comprises a head 212 and a stem 214. The femoral head 212 is configured for movable engagement with the acetabular component 205, so as to create ball-in-socket motion. The femoral stem 214 is adapted for engaging a proximal portion 215 of the patient's femur 216.

In the embodiment illustrated in FIG. 2A, a unitary sensor 305 is disposed adjacent to the acetabular component 205 of the hip implant 200. In other embodiments, unitary sensor 305 may be disposed adjacent the femoral stem 214 of the hip implant 200. In still other embodiments, unitary sensor 305 may be disposed at a plurality of locations including, but not limited to, in the bone, on the surface of the bone, near the bone, integral to an artificial joint, adjacent to an artificial joint, or near an artificial joint. The precise locations available for placement of a sensor such as unitary sensor 305 or sensor 105 may depend at least in part on the type of sensor being utilized.

Unitary sensor 305 is configured to detect and/or keep track of indicators associated with osteolytic conditions or osteolytic pre-conditions in the bone, such as temperature increases, pH increases, presence of inflammatory cytokines, and presence of certain analytes as described above.

In the embodiment illustrated in FIG. 2A, unitary sensor 305 is in wireless communication with an external receiver 325a. External receiver 325a is configured for wireless communication with the unitary sensor 305, and is adapted for retrieving and displaying, in human intelligible form, the data gathered by the unitary sensor 305.

Figure 2B:
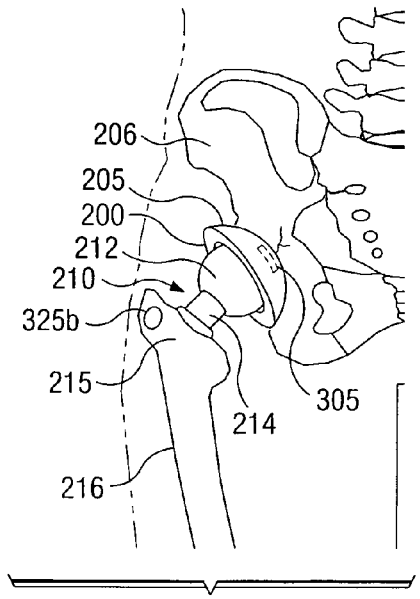
FIG. 2B is a front view of another embodiment of a detection system as described herein, which system is in use in an area where a hip prosthesis has been implanted.

Referring now to FIG. 2B, another embodiment of a detection system having a unitary sensor is illustrated. The embodiment illustrated in FIG. 2B is identical to the embodiment illustrated in FIG. 2A, with the exception of the receiver. According to the embodiment illustrated in FIG. 2B, the receiver is an internal receiver 325b, which has been implanted into the patient's body at a location near the surface of the skin. Internal receiver 325b can be embedded in soft tissue, affixed to bone, or engaged in bone, at any location that allows for the data gathered by the unitary sensor 305 to be displayed in human intelligible form. In the embodiment illustrated in FIG. 2B, it is contemplated that communication from the unitary sensor 305 to the internal receiver 325b would be wireless, however, the internal receiver 325b and the unitary sensor 305 could be wired for communication.

Figure 3A:
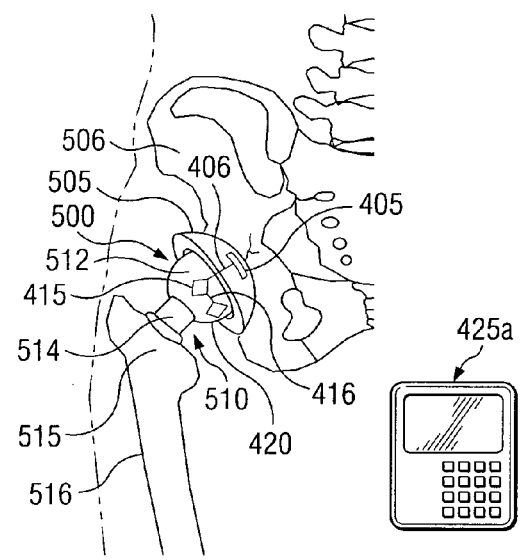
FIG. 3A is a front view of yet another embodiment of a detection system as described herein, which system is in use in an area where a hip prosthesis has been implanted.

Referring now to FIG. 3A, another embodiment of a detection system in use with a hip implant 500 is illustrated. Hip implant 500 includes an acetabular component 505, which is configured for engagement with a prepared portion of the patient's acetabulum 506, and a femoral component 510, which comprises a head 512 and a stem 514. The femoral head 512 is configured for movable engagement with the acetabular component 505, so as to create ball-in-socket motion. The femoral stem 514 is adapted for engaging a proximal portion 515 of the patient's femur 516.

A sensor 405 is disposed adjacent to the acetabular component 505, and is communicatively coupled to a transmitter 415 by internal wiring 406. The transmitter 415 is operable to receive signals from the sensor 405 indicative of osteolytic conditions or osteolytic pre-conditions in the bone, such as temperature increases, pH increases, presence of inflammatory cytokines, and presence of certain analytes, and to transmit an output signal indicative of the received signal. A power source 420 is electrically connected to the transmitter 415 to provide electrical power to the transmitter and the sensor via wiring 416. Transmitter 415 and power source 416 may be provided in a small package and positioned in soft tissue adjacent to the hip.

In the embodiment illustrated in FIG. 3A, an external receiver 425a is configured for wireless communication with the transmitter 415. In particular, external receiver 425a will receive output signals from the transmitter and display data representative of the received signals.

Figure 3B:
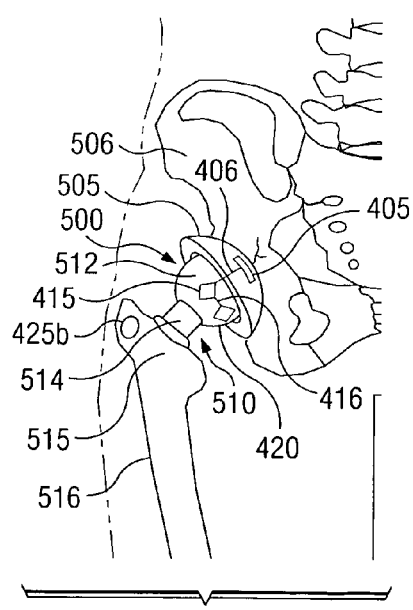
FIG. 3B is a front view of still another embodiment of a detection system as described herein, which system is in use in an area where a hip prosthesis has been implanted.

Referring now to FIG. 3B, another embodiment of a detection system is illustrated. The embodiment illustrated in FIG. 3B is identical to the embodiment illustrated in FIG. 3A, with the exception of the receiver. According to the embodiment illustrated in FIG. 3B, the receiver is an internal receiver 425b, which has been implanted into the patient's body at a location near the surface of the skin. Internal receiver 425b can be embedded in soft tissue, affixed to bone, or engaged in bone, at any location that allows for the data received from the transmitter 415 to be displayed in human intelligible form. In the embodiment illustrated in FIG. 3B, it is contemplated that communication from the transmitter 415 to the internal receiver 425b would be wireless, however, the internal receiver 425b and the transmitter 415 could be wired for communication.

In the embodiments illustrated in FIGS. 2A, 2B, 3A and 3B, the sensor of the detection system is located adjacent to the acetabular component of the hip implant. Alternatively, the sensor could be located adjacent the femoral component of the hip implant. In either embodiment, the sensor should be situated such that it is close enough to the bone surrounding the implant to detect a biological response (e.g., temperature, pH, presence of inflammatory cytokine, presence of an analyte) indicative of osteolysis or an osteolytic pre-condition. For example, in certain embodiments employing a pH sensor, the pH sensor could be in contact with the tissue of the bone surrounding the implant.

As described above, a sensor of a detection system as described herein may be disposed at a plurality of locations including, but not limited to, in the bone, on the surface of the bone, near the bone, integral to an artificial joint, adjacent to an artificial joint, or near an artificial joint. For example, the sensor of the detection system can be disposed on the exterior surface of the implant, either protruding therefrom, flush therewith, or embedded in a groove therein, and then engaged with or positioned adjacent the bone surrounding the implant so that the sensor can detect conditions indicative of osteolysis or an osteolytic pre-condition in the bone. In other embodiments, the sensor can be embedded in soft tissue surrounding the bone, or can be tethered so that it has some degree of movement, but will stay within proximity of the bone of interest.

In still other embodiments, the sensor can be directly engaged in bone surrounding an implant, for example, the sensor may be threaded and screwed into the bone, or may be secured to the bone by plates and/or spikes.

Figure 4A:
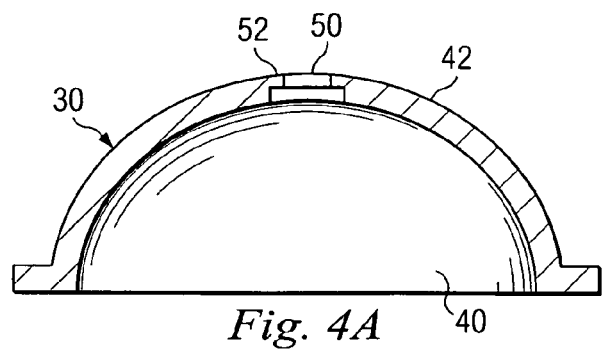
FIG. 4A is an enlarged front view of one embodiment of a hip prosthesis.
Figure 4B:
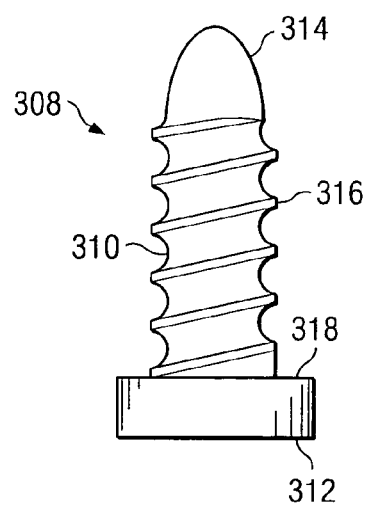
FIG. 4B is an enlarged side view of one embodiment of a sensor suitable for use in a detection system, such as the detection systems illustrated in FIGS. 2 and 3.
Figure 4C:
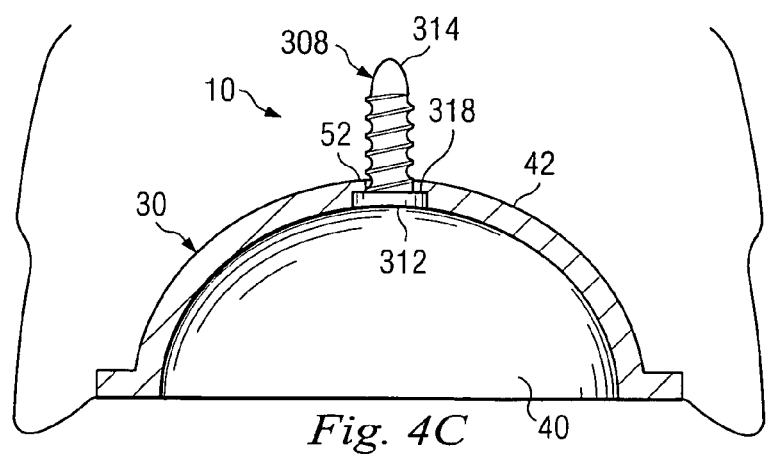
FIG. 4C is an enlarged cross-sectional side view of the sensor illustrated in FIG. 4B, engaging the hip prosthesis illustrated in FIG. 4A and adjacent bone.

Referring now to FIGS. 4A-4C, one embodiment for locating a sensor in a detection system as described herein is illustrated. FIG. 4A illustrates an acetabular component 30 of a hip implant having an opening 50 adapted to engage an insertion toll for driving the component into position. Opening 50 includes an internal flange 52 of reduced diameter. The acetabular component 30 also has a substantially spherical internal surface 40 and an exterior surface 42.

FIG. 4B illustrates a sensor 308, having a main body 310, a bone engaging portion 314, a head portion 312, and an implant engaging portion 318. The bone engaging portion 314 is adapted for being disposed within bone. To facilitate bone engagement, the exterior of the sensor may include threads 316 configured such that the sensor 308 can be screwed into engagement with bone. Implant engaging portion 318 is adapted for engaging internal flange 52 of opening 50 of the acetabular component 30. The inner surface 40 of the acetabular component 30 is adapted for movably engaging a femoral head (not illustrated) of the hip implant. Flange portion 52 is recessed with respect to inner surface 40 of the acetabular component 30 so that when implant engaging portion 318 is engaged with flange 52, the head 312 substantially aligns with inner surface 40 and does not inhibit movable engagement between the femoral head and the inner surface.

FIG. 4C illustrates sensor 308 engaged with the bone 10 and the acetabular component 205. External surface 42 of the acetabular component 30 also engages the bone 10.

Figure 5A:
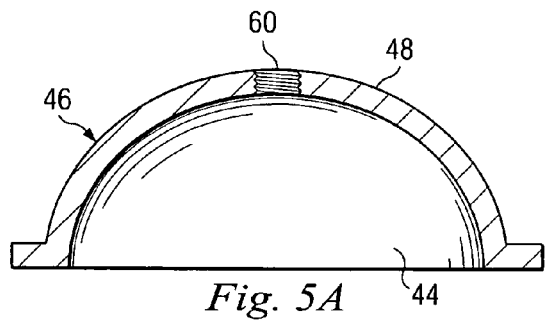
FIG. 5A is an enlarged front view of another embodiment of a hip prosthesis.
Figure 5B:
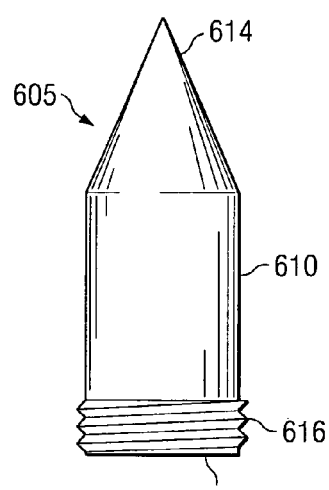
FIG. 5B is an enlarged side view of another embodiment of a sensor suitable for use in a detection system, such as the detection systems illustrated in FIGS. 2 and 3.
Figure 5C:
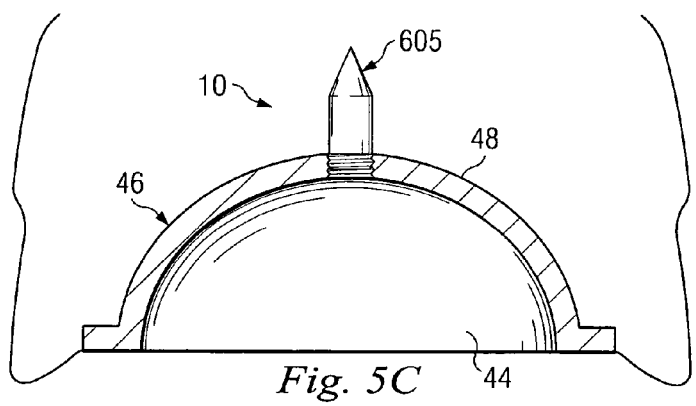
FIG. 5C is an enlarged cross-sectional side view of the sensor illustrated in FIG. 5B, engaging the hip prosthesis illustrated in FIG. 5A and adjacent bone.

Referring now to FIGS. 5A-5C, another embodiment for locating a sensor in a detection system as described herein is illustrated. The sensor 605 includes a main body 610, an implant engaging portion 612, and a bone engaging portion 614, which, in certain embodiments, may be substantially similar to a bone nail. The implant engaging portion 612 includes threads 616, which are adapted for engaging a threaded portion of an implant. For example, threads 616 may be adapted for engaging a threaded driver portion 60 of an acetabular component 205. An inner surface 44 of an acetabular component 46 is adapted for movable engagement with a femoral head (not illustrated) of a hip implant. The implant engagement portion 612 and the threaded driver portion 60 are configured such that when the two portions are threaded together the movable engagement between the femoral head and the inner surface 44 is not inhibited. FIG. 5C shows sensor 605 engaged with the bone 10 and the acetabular component 46. An external surface 48 of the acetabular component 46 also engages the bone.

Figure 6:
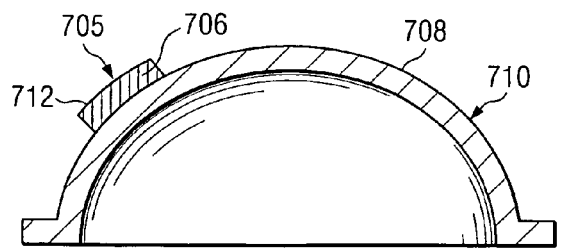
FIG. 6 is an enlarged cross sectional view of another embodiment of a sensor suitable for use in a detection system as described herein, which sensor is disposed on an external surface of a prosthesis.

Referring now to FIG. 6, yet another embodiment for locating a sensor in a detection system as described herein is illustrated. FIG. 6 illustrates a sensor 705, attached at a surface 706 to a surface 708 of an acetabular component 710 of a hip implant. The opposing surface 712 of the sensor 707 is adapted for engaging adjacent bone, or physical contact with adjacent bone. It is contemplated that the sensor 707 may be associated with surface 706 without being fixedly mounted. However, it is also contemplated that the sensor 707 may be attached to the surface 706 by any reliable means. In some embodiments, the sensor 707 can be attached to the surface 706 of the acetabular component 710 by a polymethylmethacrylate (PMMA) cement, cyanoacrylate, fibrin glue, or other biocompatible glues.

Although the figures provided illustrate a detection system in use with a hip implant, a detection system as described herein could also be used with a knee implant, vertebral implant, shoulder implant, etc. Moreover, although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "inner," "outer," "bottom," "left," "right," "anterior," "posterior," "superior," "inferior," "upper," and "lower" are for illustrative purposes only and can be varied within the scope of the disclosure. In the claims, means-plus-function clauses are intended to cover the elements described herein as performing the recited function and not only structural equivalents, but also equivalent elements.

What is claimed is:

1. A detection system for detecting a condition of a bone comprising:
   a sensor capable of operating in vivo to detect a cytokine associated with a condition of a bone and to generate a signal representative of a level of the detected cytokine, the sensor configured to be positioned in direct contact with the bone and extending through and in engagement with an artificial implant, the artificial implant defining an opening such that the sensor extends through the opening and into the bone, the sensor having an outer surface configured to detect the cytokine, the outer surface including a bone engaging portion configured for disposal within the bone and for directly detecting the cytokine in the bone, the bone engaging portion extending from an outer surface of the artificial implant, and the sensor having an implant portion having an end surface being aligned with an inner surface of the artificial implant;
   a transmitter operable to receive the signal from the sensor and transmit the signal;
   a receiver operable to receive the signal from the transmitter and to enable a human intelligible display representative of the signal;
   at least one control sensor capable of operating in vivo at an area remote from the sensor, and operable to detect a condition in a bone at the remote area and to generate a signal representative of the detected condition; and
   a signal processor operable to receive and compare signals generated by the sensor and signals generated by the at least one control sensor, and operable to send a signal to the transmitter when a signal received from the sensor deviates from a signal received from the at least one control sensor.

2. The detection system of claim 1 wherein the cytokine detected is present in the bone.

3. The detection system of claim 1 wherein the cytokine detected is adjacent to the bone.

4. The detection system of claim 1 wherein the sensor is operable to detect a cytokine selected from the group consisting of TNF, IL-1, and IL-6.

5. The detection system of claim 1 wherein the signal processor is operable to receive signals from the sensor and to generate a baseline representative of the detected level of cytokine, and to send a signal to the transmitter when a signal received from the sensor deviates from the baseline.

6. The detection system of claim 1 further comprising:
   a wireless telemetry circuit configured for transmitting the signal from the transmitter to the receiver.

7. The detection system of claim 1 further comprising:
   a power source electrically connected to at least one of the sensor, the transmitter and the receiver.

8. The detection system of claim 1 wherein the receiver comprises:
   a signal processor operable to convert the signal to a displayable format and to transmit the converted signal; and
   an indicator operable to receive the converted signal and provide a human intelligible display representative of the converted signal.

9. The detection system of claim 1 wherein the receiver comprises:
  analysis circuitry operable to compare a signal received from the transmitter to a control, and to generate a signal when the signal received from the transmitter exceeds the control; and
  an indicator operable to receive the signal generated by the analysis circuitry and to provide a human intelligible display representative of the signal.

10. The detection system of claim 1 further comprising:
  an indicator operable to provide a human intelligible display representative of the signal received by the receiver.

11. The detection system of claim 1 wherein the sensor, the signal processor, and the transmitter are combined into a unitary structure.

12. The detection system of claim 11, wherein the unitary structure is capable of operating entirely in vivo.

13. The detection system of claim 1, wherein at least a portion of the inner surface of the artificial implant has a spherical configuration and the spherical portion is aligned with the end surface of the implant portion.

14. The detection system of claim 1 wherein a second sensor is adjacent the bone.

15. The detection system of claim 1 wherein the artificial implant has a recessed flange portion adapted for engagement with the implant portion of the sensor.

16. The detection system of claim 15, wherein the implant is for use in at least one of an ankle, a knee, a hip, a spine, a shoulder, an elbow, a wrist, and a jaw.

17. The detection system of claim 1 wherein the receiver is capable of operating in vivo.

18. The detection system of claim 1 wherein the receiver is capable of operating ex vivo.

19. A detection system for detecting a condition of a bone comprising:
  a sensor located in vivo in direct contact with the bone and operable to detect an analyte associated with the onset of an osteolytic condition in the bone and generate a signal representative of a level of the detected analyte, the sensor having an outer surface configured to detect the analyte, the outer surface including a bone engaging portion configured for disposal within the bone and for directly detecting the analyte in the bone, the bone engaging portion extending from an outer surface of an artificial implant, the artificial implant defining an opening such that the sensor extends through the opening and into the bone, and the sensor having an implant portion being aligned with a spherical inner surface of the artificial implant;
  a first signal processor operable to receive a signal from the sensor and to transmit the signal;
  a transmitter operable to receive the signal from the first signal processor and to transmit the signal;
  a receiver operable to receive the signal from the transmitter and to transmit the signal;
  a second signal processor operable to receive the signal from the receiver and to transmit the signal;
  an indicator operable to receive the signal from the second signal processor and provide a human intelligible display representative of the signal;
  at least one control sensor located in vivo at an area remote from the sensor, and operable to detect a condition in a bone at the remote area and to generate a signal representative of the detected condition; and
  analysis circuitry operable to compare a signal received from the transmitter to a control, and to send a signal to the indicator that is either implanted close to the surface of skin or ex vivo so that a signal from the indicator can be observed either through the skin or external to a body of a patient when the signal received from the transmitter exceeds the control;
  wherein the first signal processor is operable to receive and compare signals generated by the sensor and signals generated by the at least one control sensor, and to send a signal to the transmitter when a signal received from the sensor deviates from a signal received from the at least one control sensor.

20. The detection system of claim 19, wherein the first signal processor is located in vivo.

21. The detection system of claim 19 wherein the sensor is operable to detect an analyte selected from the group consisting of calcium ions, phosphate ions, and matrix metalloproteinases.

22. The detection system of claim 19 wherein the first signal processor uses the signals received from the sensor to generate a baseline representative of the detected level of analyte, and sends a signal to the transmitter when a signal received from the sensor deviates from the baseline.

23. The detection system of claim 19 wherein the sensor, the first signal processor and the transmitter are combined into a unitary structure.

24. The detection system of claim 19 wherein the receiver, the second signal processor and the indicator are combined into a unitary structure.

25. The detection system of claim 19 wherein the receiver is in vivo.

26. The detection system of claim 19 wherein the receiver is ex vivo.

27. A detection system for detecting a condition of a bone comprising:
  an in vivo sensor adapted to detect a cytokine in the bone and generate a signal representative of the detected cytokine, the sensor having an outer surface configured to detect the cytokine, the outer surface including a bone engaging portion configured for disposal within the bone and for directly detecting the cytokine in the bone, the bone engaging portion extending from an outer surface of an artificial implant, the artificial implant defining an opening such that the sensor extends through the opening and into the bone, and the sensor having an implant portion having an end surface being aligned with an inner surface of the artificial implant;
  a transmitter operable to receive the signal from the sensor and transmit the signal;
  a receiver operable to receive the signal from the transmitter and to enable a human intelligible display representative of the signal;
  at least one control sensor located in vivo at an area remote from the sensor, and operable to detect a condition of a bone at the remote area and to generate a signal representative of the detected condition; and
  a signal processor operable to receive and compare signals generated by the sensor and signals generated by the at least one control sensor, and operable to send a signal to the transmitter when a signal received from the sensor deviates from a signal received from the at least one control sensor.

28. The detection system of claim 27, wherein the signal processor is located in vivo.

29. The detection system of claim 27, wherein the opening has a recessed flange portion configured to receive the implant portion in a mating engagement such that the end surface of the implant portion is aligned with the inner surface of the artificial implant.

30. The detection system of claim 27, wherein at least a portion of the inner surface of the artificial implant has a spherical configuration and the spherical portion is aligned with the end surface of the implant portion.

* * * * *